United States Patent
Sherry

(10) Patent No.: US 7,806,876 B2
(45) Date of Patent: *Oct. 5, 2010

(54) IMPLANTABLE VASCULAR ACCESS DEVICE

(75) Inventor: John Sherry, Needham, MA (US)

(73) Assignee: Navilyst Medical, Inc., Marlborough, MA (US)

( * ) Notice: Subject to any disclaimer, the term of this patent is extended or adjusted under 35 U.S.C. 154(b) by 337 days.

This patent is subject to a terminal disclaimer.

(21) Appl. No.: 11/748,749

(22) Filed: May 15, 2007

(65) Prior Publication Data

US 2007/0293823 A1    Dec. 20, 2007

Related U.S. Application Data

(63) Continuation of application No. 10/342,913, filed on Jan. 15, 2003, now Pat. No. 7,252,649, which is a continuation of application No. 09/957,619, filed on Sep. 20, 2001, now Pat. No. 6,540,717, which is a continuation of application No. 09/398,887, filed on Sep. 20, 1999, now Pat. No. 6,319,226.

(51) Int. Cl.
*A61M 37/00* (2006.01)

(52) U.S. Cl. ............................. 604/288.03; 604/288.01; 604/288.04

(58) Field of Classification Search .................. 604/256, 604/288.01–288.04
See application file for complete search history.

(56) References Cited

U.S. PATENT DOCUMENTS 5,931,801 A * 8/1999 Burbank et al. ............ 604/4.01
6,319,226 B1 * 11/2001 Sherry ..................... 604/93.01

* cited by examiner

*Primary Examiner*—Nicholas D Lucchesi
*Assistant Examiner*—Leah Stohr
(74) *Attorney, Agent, or Firm*—Bingham McCutchen LLP

(57) ABSTRACT

An implantable vascular access device includes a housing having an inlet, an outlet, an interior chamber defined therein and a valve positioned between the inlet and the interior chamber. The valve is subcutaneously manipulated between an open position, in which fluid can flow between the inlet and the interior chamber, and a closed position in which the valve occludes the inlet. The device may include any combination of multiple inlets, outlets and/or interior chambers. In the preferred embodiment, the housing includes two separate interior chambers suitable for the inflow and outflow of a typical hemodialysis procedure. A method for accessing a vascular structure is provided which includes the steps of subcutaneously implanting the device connecting one end of a cannula to the outlet of the device and another end of the cannula to a selected vascular structure. The valve of the device is manipulated to permit fluid communication between the inlet of the device and the selected vascular structure. A needle is introduced through the inlet opening to access the selected vascular structure.

20 Claims, 3 Drawing Sheets

IMPLANTABLE VASCULAR ACCESS DEVICE

PRIORITY CLAIM

This application is a Continuation application of U.S. patent application Ser. No. 10/342,913 filed on Jan. 15, 2003 now U.S. Pat. No. 7,252,649 entitled "Implantable Vascular Access Device" which is a Continuation of U.S. patent application Ser. No. 09/957,619 filed on Sep. 20, 2001 now U.S. Pat. No. 6,540,717 entitled "Implantable Vascular Access Device" and which is a Continuation of U.S. patent application Ser. No. 09/398,887 filed on Sep. 20, 1999 now U.S. Pat. No. 6,319,226 entitled "Implantable Vascular Access Device". The entire disclosures of these prior applications are considered as being part of the disclosure of the accompanying application and hereby expressly incorporated by reference herein.

BACKGROUND OF THE INVENTION

1. Field Of Invention

The present invention relates to implantable vascular access devices used in the delivery and/or withdrawal of fluids to and from the body and more particularly relates to a self-sealing device which permits intermittent vascular access.

2. Description Of The Prior Art

Conventional vascular access devices are surgically implanted under the skin to allow for intermittent access to a selected vascular structure, such as an artery or a vein, for introducing and/or withdrawing fluids to and from the selected vascular structure. Typically, such devices generally include an interior chamber having an outlet opening connected via a cannula to a vascular structure within the body and a penetrable membrane which serves as a cover for the interior chamber of the device. The penetrable membrane or septum is comprised of a material, such as silicone rubber, which automatically reseals itself after being penetrated by a hypodermic needle or a needle introduced catheter.

In operation, a needle passes through the skin and through the penetrable membrane into the interior chamber allowing fluid to be injected into the chamber and expelled through the cannula into the selected vascular structure or, conversely, fluid may be withdrawn. The advantages of an implantable device over acute catheter procedures include reduced infection, easier patient maintenance and improved aesthetics. Typical implantable vascular access devices are shown in U.S. Pat. No. 5,318,545 to Tucker and U.S. Pat. No. 5,755,780 to Finch, Jr. et al.

The advancement of modern hemodialysis procedures have brought with it the development of vascular access devices for the purpose of acquiring and returning large quantities of blood for passage through a hemodialysis unit. To facilitate adequate dialysis flow rates, relatively large diameter needles and/or catheters in the range of 14 gauge or higher are required. A major drawback of conventional vascular access devices, particularly those used in hemodialysis procedures, is the deterioration of the rubber membranes as a result of repeated penetration with such large gauge needles. Additionally, typical vascular access devices provide for only one needle port resulting in chronic breach of the skin at the same location. This in turn results in increased skin trauma and possible infection.

Accordingly, it is desirable to provide a vascular access device which can withstand multiple insertions with a large diameter needle and which provides reduced skin trauma and easier patient maintenance.

SUMMARY OF THE INVENTION

It is an object of the present invention to provide a vascular access device which can withstand a high number of large gauge needle insertions without deterioration.

It is another object of the present invention to provide a vascular access device which is easily subcutaneously manipulated and which prevents the escape of fluids from the device.

It is yet another object of the present invention to provide a vascular access device having multiple needle ports thereby reducing the skin trauma caused by repeated needle sticks at the same location.

It is still a further object of the present invention to provide a vascular access device suitable for hemodialysis procedures which incorporates two interior chambers into a single body.

In accordance with one form of the present invention, a vascular access device generally includes a housing having an inlet, an outlet, an interior chamber defined therein and a valve positioned between the inlet and the interior chamber. The valve is movable between an open position, in which fluid can flow between the inlet and the interior chamber, and a closed position in which the valve occludes the inlet. Preferably the valve comprises an elongate member having a through-hole formed therein which aligns with the inlet when the valve is in the open position. One or both ends of the elongate member protrudes through the housing and is palpable through the skin of the patient. The elongate member is resiliently urged to its closed position by a spring and is opened by subcutaneously pressing the end of the member protruding through the housing.

The device includes a cannula having a proximal end connected to the outlet of the housing and a distal end connected to a selected vascular structure. In one embodiment, the distal end of the cannula includes a distal valve positioned within the cannula adjacent the outlet of the cannula. The distal valve is connected to the housing valve and is preferably a tubular member having an outer wall and an interior passage. Along with the housing valve, the distal valve is simultaneously movable within the cannula between an open position in which fluid can flow between the housing outlet and the cannula outlet through the interior passage of the tubular member and a closed position in which the outer wall of the tubular member occludes the cannula outlet. The tubular member is resiliently urged to its closed position by a spring attached to the cannula.

The present invention may include any combination of multiple inlets, outlets and/or interior chambers. In the preferred embodiment, the housing includes two separate interior chambers suitable for the inflow and outflow of a typical hemodialysis procedure. The device further includes multiple inlets in fluid communication with each interior chamber. Several elongate members are moved simultaneously to an open position by a single push button protruding through the outer surface of the housing. Each elongate member includes through-holes which are aligned with respective inlets when the push button is depressed to move the elongate members to their open position. When the button is released, a spring urges the elongate members to their closed position thereby occluding the inlets. Each interior chamber is in fluid communication with an outlet which is connected to a selected vascular structure by means of a cannula for permitting fluid communication between the vascular structure and the interior chamber of the device.

A method for accessing a vascular structure is provided which includes the steps of surgically implanting a device as described above, connecting one end of a cannula to the outlet of the device and another end of the cannula to a selected vascular structure, subcutaneously manipulating the valve of the device for permitting fluid communication between the inlet of the device and the selected vascular structure and introducing a needle or a needle-introduced catheter through the inlet opening to access the selected vascular structure.

A preferred form of the vascular access device, as well as other embodiments, objects, features and advantages of this invention will be apparent from the following detailed description of illustrative embodiments thereof which is to be read in conjunction with the accompanying drawings.

DETAILED DESCRIPTION OF THE PREFERRED EMBODIMENTS

Figure 1A:
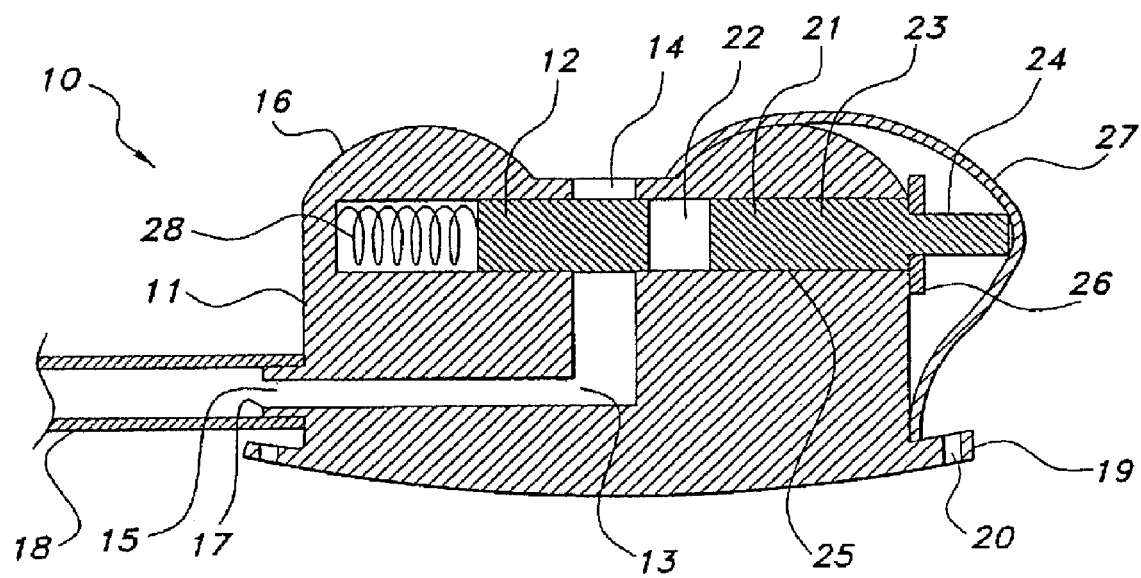
FIGS. 1A and 1B are cross-sectional views of the vascular access device formed in accordance with the present invention showing the valve in its closed and open positions, respectively.
Figure 1B:
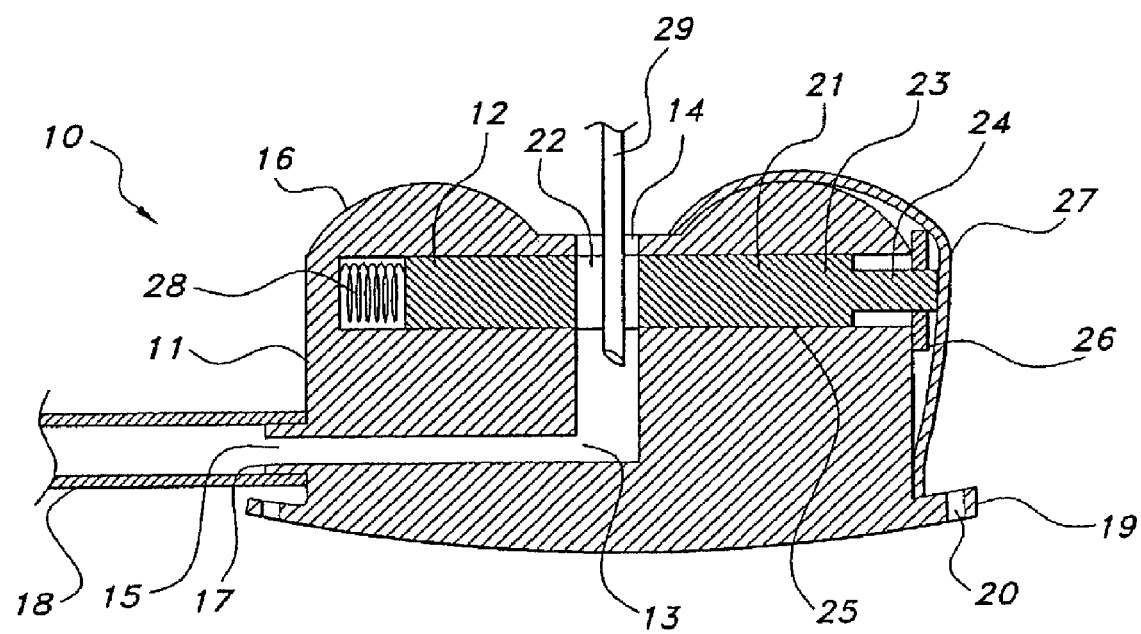

Referring to FIGS. 1A and 1B, an implantable vascular access device formed in accordance with the present invention is shown. The vascular access device 10 is designed to be surgically implanted under the skin and generally includes a housing 11 and a valve 12. The housing 11 and the valve 12 may be made from any suitable biocompatible material possessing sufficient hardness to resist being damaged or gouged by needles or other devices which will be repeatedly inserted into the device. Plastic constructions are advantageous in that they are inexpensive to fabricate utilizing conventional molding techniques and are available in a variety of biocompatible materials. Surgical metals, however, are also suitable.

The housing 11 includes an interior chamber 13 formed therein, and an inlet 14 and an outlet 15 extending through an external surface 16 of the housing and communicating with the interior chamber. The outlet 15 may be formed with a cuff 17 to facilitate connection to a cannula 18. The opposite end (not shown) of the cannula is connected or grafted to a selected vascular structure (e.g. an artery or a vein) in a conventional manner. The housing 11 also includes a peripheral rim 19 having apertures 20 for securing the device to fascia underlying the skin by means of sutures threaded through the peripheral apertures.

The valve 12 preferably comprises an elongate member 21 having a transverse bore or through-hole 22 formed in a body portion 23 thereof. The elongate member 21 further includes a neck portion 24 which protrudes through the external surface 16 of the housing. The elongate member 21 is supported within a bore 25 formed in the housing 11 and is retained within the housing by a retaining clip 26 fixed to the external surface 16 of the housing. The valve 12 may be positioned anywhere along the interior chamber 13 between the housing inlet 14 and the housing outlet 15. To maintain the proper orientation of the elongate member 21 with respect to the interior chamber 13, the neck portion 24 and/or the body portion 23 is formed with a non-circular cross-section which prevents the elongate member from rotating when fitted in close sliding relationship within the correspondingly sized bore 25 and retaining clip 26. A deformable element 27 fixed to the external surface 16 of the housing 11 is preferably provided over the protruding neck portion 24 of the elongate member 21. Sealing rings (not shown) may also be provided on the elongate member 21 to prevent tissue ingrowth and/or leakage to and from the bore 25.

A spring 28 is positioned within the bore 25 at the end of the elongate member 21 opposite the neck portion 24. The spring 28 is also made from a biocompatible material and is captured within the bore 25 for resiliently urging the elongate member 21 to its closed position, i.e., to the right as shown in FIGS. 1A and 1B. Although a spring is preferred, other biasing devices may also be utilized for resiliently urging the elongate member 21 to its closed position. For example, the spring 28 may be removed and the bore 25 may be sized to form a compression chamber behind the elongate member 21 wherein the trapped air pressure acts upon the body portion 23 of the elongate member to urge it to its closed position.

In use, the vascular access device 10 is surgically implanted such that it is entirely subcutaneous. In its normally closed position, the body portion 23 of the elongate member 21 blocks or occludes the inlet opening 14 thereby preventing fluid communication between the inlet and the interior chamber 13. When the protruding end of the body portion 23 is subcutaneously depressed, the elongate member 21 moves to its open position in which the transverse through-hole 22 aligns with the inlet opening 14 thereby permitting fluid communication between the inlet opening and the interior chamber 13 through the elongate member. When the valve 12 is in its open position, a needle 29 or a needle-introduced catheter may be percutaneously inserted through the inlet 14 into the interior chamber 13 to introduce or withdraw fluid from the selected vascular structure via the cannula 18. Once the needle 29 is inserted, the needle will hold the elongate member 21 in its open position thereby allowing the protruding end of the body portion 23 to be released. Once the needle 29 is removed, the spring 25 will automatically return the elongate member 21 to its closed position in which the inlet opening 14 is again occluded and blood reflux is prevented.

Figure 2A:
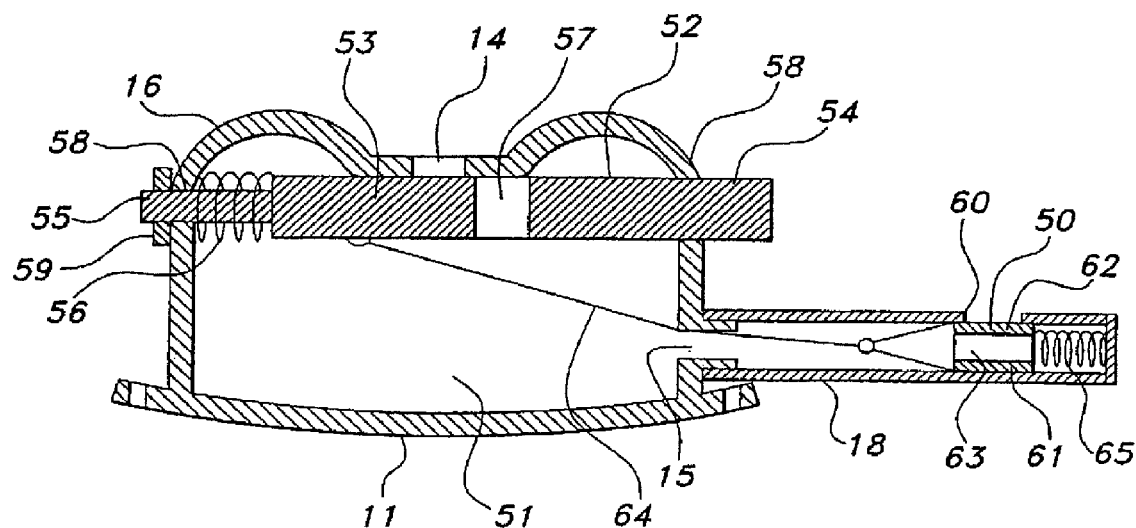
FIGS. 2A and 2B are cross-sectional views of an alternate embodiment of the device including a distal cannula valve and showing the valves in their closed and open positions, respectively.
Figure 2B:
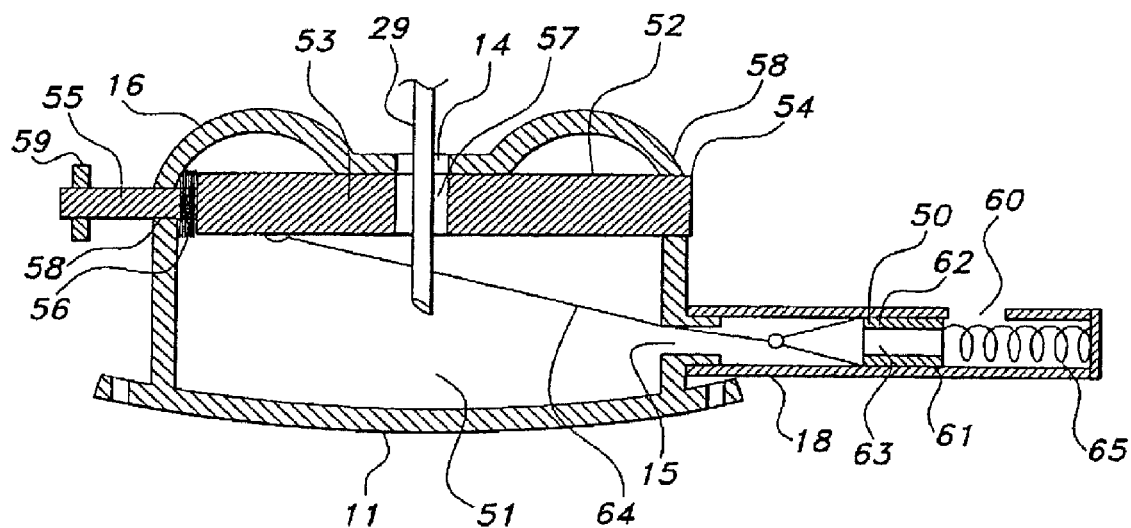

FIGS. 2A and 2B show an alternate embodiment of the device wherein a cannula valve 50 is also provided. In this embodiment, the housing 11 includes an interior chamber 51 formed therein as opposed to the interior chamber 13 described above. The housing valve 52 comprises an elongate member 53 having a body portion 54 and a neck portion 55 for accommodating a spring 56. A transverse bore or through-hole 57 is formed in the body portion 54 to provide fluid communication between the inlet 14 and the interior chamber 51 when the elongate member 53 is in its open position. The elongate member 53 is supported within opposite support holes 58 formed in the housing 11 such that both the body portion 54 and the neck portion 55 protrude through the housing. The neck portion 55 and/or the body portion 54 is formed with a non-circular cross-section which when fitted in a correspondingly sized support hole 58 maintains the elongate member 53 in its proper orientation. The elongate member 53 is retained within the housing by a retaining clip 59 fixed to the protruding neck portion 55 and deformable skins (not shown) are preferably provided over both protruding portions to prevent tissue ingrowth as described above.

The cannula 18 includes a cannula valve 50 positioned within the cannula adjacent a cannula outlet 60 for selectively permitting fluid flow between the housing outlet 15 and the selected vascular structure. The cannula valve 50 comprises a biocompatible tubular member 61 having an outer wall 62 and an interior passage 63. The tubular member 61 is connected to the housing valve 12 via a taut wire 64 such that manipulation of the housing valve simultaneously activates the cannula valve. A tension spring 65 is provided at the distal end of the cannula 18 to resiliently urge the tubular member 61 to a closed position wherein the outer wall 62 of the tubular member occludes the cannula outlet 60.

In use, depressing the body portion 54 of the elongate member 53 of the housing valve 52 moves the housing valve to its open position, i.e., to the left as shown in FIGS. 2A and 2B, thereby simultaneously pulling the cannula valve 50 to an open position via the wire 64. In the open position, the outer wall 62 of the tubular member 61 no longer occludes the cannula outlet 60 and fluid may flow through the interior passage 63 of the tubular member between the housing outlet 15 and the cannula outlet. When the housing valve 12 is released, the tension spring 65 returns the tubular member 61 to its closed position whereby the outer wall 62 of the tubular member again occludes the cannula outlet 60.

Figure 3:
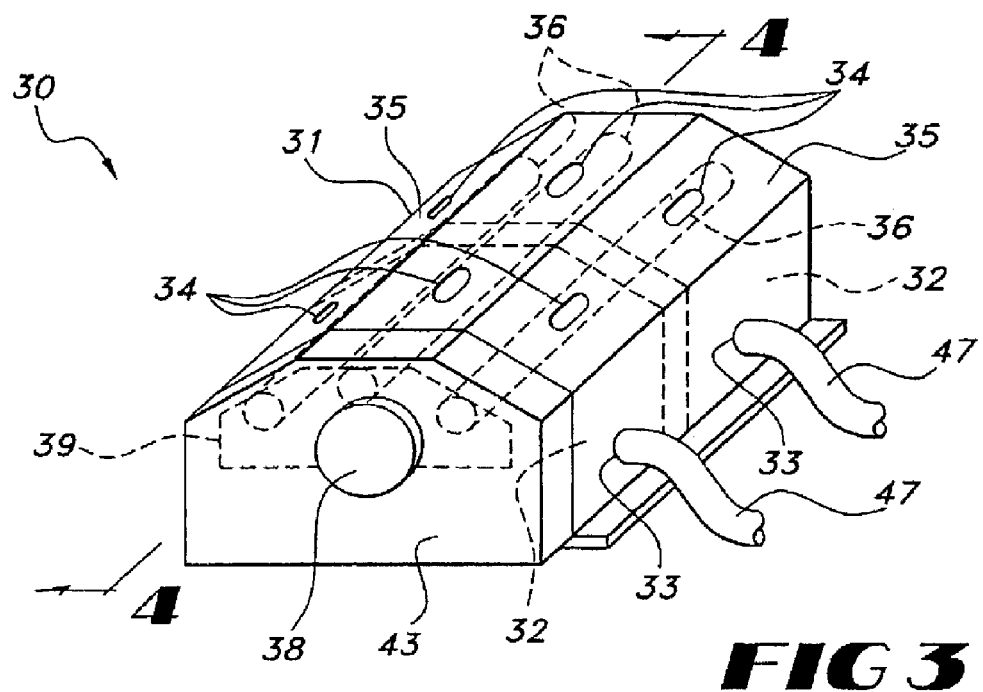
FIG. 3 a perspective view of the preferred embodiment of the device shown in FIGS. 1A and 1B.
Figure 4:
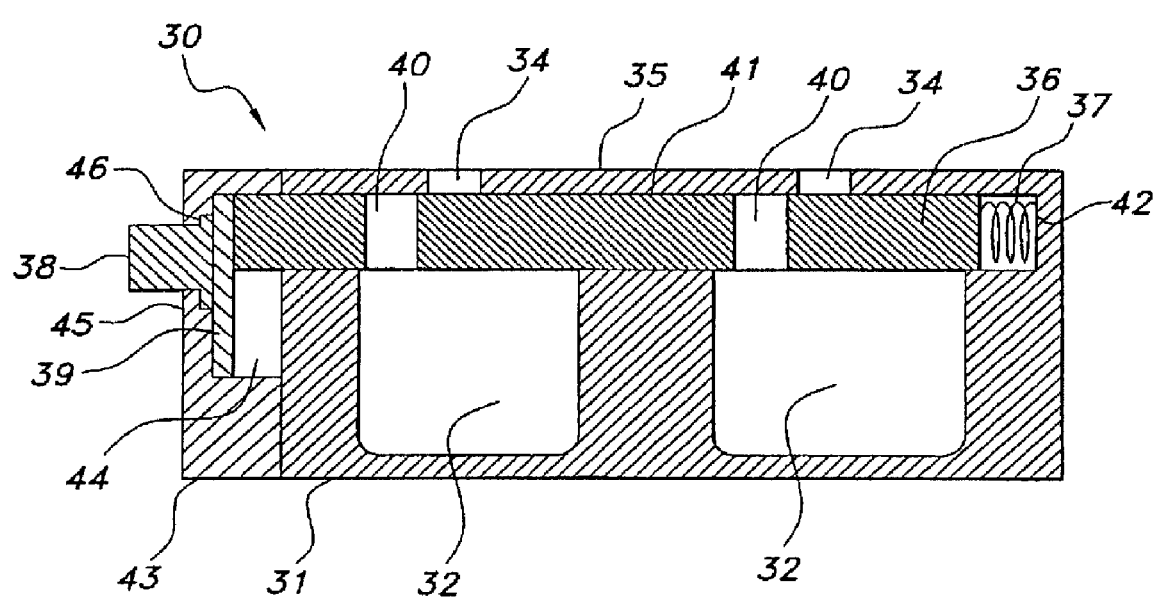
FIG. 4 is a cross-sectional view of the device shown in FIG. 3 taken along the line 4-4.

Referring now to FIGS. 3 and 4, a preferred form of the implantable vascular access device 30 is shown. The multi-port device 30 shown in FIGS. 3 and 4 includes a housing 31 formed with two separate interior chambers 32, an outlet 33 in fluid communication with each interior chamber and a plurality of inlets 34. The housing 31 shown in FIGS. 3 and 4 includes three external access surfaces 35 each with a pair of inlets 34 which communicate with a respective interior chamber 32. However, any geometric configuration for the housing, such as additional access surfaces, additional interior chambers or additional inlets may be utilized.

The multi-port device 30 includes a valve which comprises three elongate members 36 each having a spring 37 fixed at one end thereof and a push button 38 with a push plate 39 adjacent the other end. The elongate members 36 are formed with transverse through-holes 40, as described above, and are slidably supported in longitudinal bores 41 formed in the housing. The springs 37 are captured between the elongate members 36 and the bottom walls 42 of the longitudinal bores 41 formed at one end of the housing 31. An end cap 43 is fixed to the opposite end of the housing 31 for retaining the push button 38 and the push plate 39. The end cap 43 is formed with a recess 44 for retaining the push plate 39 and a counter bored opening 45 through which the push button 38 protrudes. The push button 38 is formed with a shoulder portion 46 which is retained by the counter bored opening 45 so that the push button is held within the end cap 43. The depth of the recess 44 allows the push plate 39 to travel a predetermined distance when the push button 38 is depressed.

Operation of the multi-port device 30 is similar to that as described above. The springs 37 resiliently urge each of the individual elongate members 36 into their normally closed position in which the elongate members occlude the inlet openings 34. When the push button 38 is subcutaneously depressed, the elongate members 36 are simultaneously moved to their open position by the push plate 39 (i.e., to the right as shown in FIG. 3) wherein the transverse through-holes 40 of the elongate members align with respective inlet openings 34. Again, the elongate members 36 may be formed with non-circular cross-sections so that their proper orientation with respect to the inlets 34 is maintained. Once the elongate members 36 are moved to their open position any one or more of the inlets 34 may be accessed with a needle for withdrawing or introducing fluid through the interior chambers 32. In a typical hemodialysis procedure, an infusion needle is inserted through an inlet 34 into one of the interior chambers 32 and an aspiration needle is inserted through another inlet into the other separate chamber. The interior chambers are in fluid communication with at least one selected vascular structure by means of the cannulas 47, as described above. Again, once the needles are inserted the push button 38 may be released and upon removing the needle the springs 37 automatically urge the elongate members 36 back to their normally closed position. Preferably, needles should be inserted in corresponding pairs of inlets 34 on the same access surface 35 so that when the push button 38 is released the remaining elongate members not being accessed will return to their closed position.

As a result of the present invention, a multi-port vascular access device is provided which can withstand numerous needle insertions without deterioration. Additionally, the multi-port design allows for needle insertion at different locations on the skin thereby allowing the skin more time to heal before reinsertion of a needle. Furthermore, the dual interior chamber design of the present invention is particularly suitable for hemodialysis procedures requiring simultaneous inflow and outflow.

Although the illustrative embodiments of the present invention have been described herein with reference to the accompanying drawings, it is to be understood that the invention is not limited to those precise embodiments, and that various other changes and/or modifications may be effected therein by one skilled in the art without departing from the scope or spirit of the invention, and it is intended to claim all such changes and/or modifications as fall within the scope of the invention.

What is claimed is:

1. A surgically implantable device, comprising:
   a housing having an inlet opening, an outlet opening and an interior conduit defined therein between the inlet opening and the outlet opening; and
   a manipulatable housing valve positioned between the inlet opening and the outlet opening for selectively permitting fluid communication between the inlet opening and the outlet opening, the housing valve comprising an elongate member supported within the housing, the elongate member being movable between an open position, in which fluid communication is permitted between the inlet opening and the outlet opening, and a closed position, in which the elongate member occludes fluid communication between the inlet opening and the outlet opening,
   wherein at least one end of the elongate member protrudes through an external surface of the housing, the at least one end of the elongate member being subcutaneously manipulatable for moving the elongate member between the open and closed positions,
   wherein the elongate member includes a transverse bore formed therethrough, the bore aligning with the interior conduit when the elongate member is in the open position for permitting fluid communication between the inlet opening and the outlet opening,
   wherein the elongate member has a non-circular cross section, and
   wherein the elongate member is supported within a support hole of the housing that has a non-circular cross-section corresponding in shape to that of the elongate member, the correspondingly shaped cross-sections of the elongate member and the support hole preventing a misalignment of the transverse bore and the interior conduit in the open position.

2. The device of claim 1, further comprising:
   a biasing device adjacent the elongate member for resiliently urging the elongate member to the closed position.

3. The device of claim 2, wherein the biasing device included at least one spring.

4. The device of claim 2, wherein the biasing device included a compression chamber.

5. The device of claim 1, further comprising:
a cannula having a proximal end connected to the housing outlet opening and a distal end connectable to a selected vascular structure.

6. The device of claim 5, wherein the distal end of the cannula includes a manipulatable distal valve positioned adjacent a cannula outlet for selectively permitting fluid communication between the housing outlet opening and the cannula outlet.

7. The device of claim 6, wherein the distal valve is connected to the housing valve whereby manipulation of the housing valve simultaneously activates the distal valve.

8. The device of claim 6, wherein the distal valve comprises a tubular member having an outer wall and an interior passage, the tubular member being movable within the cannula between an open position, in which fluid communication is permitted between the housing outlet opening and the cannula outlet through the interior passage of the tubular member, and a closed position, in which the outer wall of the tubular member occludes the cannula outlet thereby preventing fluid communication between the housing outlet opening and the cannula outlet.

9. The device of claim 8, further comprising a biasing device adjacent the tubular member for resiliently urging the tubular member to the closed position.

10. A surgically implantable device, comprising:
a housing having an inlet opening, an outlet opening and an interior conduit defined therein between the inlet opening and the outlet opening; and
a manipulatable housing valve positioned between the inlet opening and the outlet opening for selectively permitting fluid communication between the inlet opening and the outlet opening,
wherein the housing valve includes an elongate member supported within the housing, the elongate member being movable between an open position, in which fluid communication is permitted between the inlet opening and the outlet opening, and a closed position, in which the elongate member occludes fluid communication between the inlet opening and the outlet opening,
wherein at least one end of the elongate member protrudes through an external surface of the housing, the at least one end of the elongate member being subcutaneously manipulatable for moving the elongate member between the open and closed positions,
wherein the elongate member includes a transverse bore formed therethrough, the bore aligning with the interior conduit when the elongate member is in the open position for permitting fluid communication between the inlet opening and the outlet opening,
wherein the elongate member has a non-circular cross section, and
wherein the elongate member is inserted through an opening of a retaining clip attached to the housing, the opening of the retaining having a non-circular cross-section corresponding in shape to that of the elongate member, the correspondingly shaped cross-sections of the elongate member and the retaining clip opening preventing a misalignment of the transverse bore and the interior conduit in the open position.

11. The device of claim 10, further comprising:
a biasing device adjacent the elongate member for resiliently urging the elongate member to the closed position.

12. The device of claim 11, wherein the biasing device comprises at least one spring.

13. The device of claim 11, wherein the biasing device comprises a compression chamber.

14. The device of claim 10, further comprising:
a cannula having a proximal end connected to the housing outlet opening and a distal end connectable to a selected vascular structure.

15. The device of claim 14, wherein the distal end of the cannula includes a manipulatable distal valve positioned adjacent a cannula outlet for selectively permitting fluid communication between the housing outlet opening and the cannula outlet.

16. The device of claim 15, wherein the distal valve is connected to the housing valve whereby manipulation of the housing valve simultaneously activates the distal valve.

17. The device of claim 15, wherein the distal valve comprises a tubular member having an outer wall and an interior passage, the tubular member being movable within the cannula between an open position, in which fluid communication is permitted between the housing outlet opening and the cannula outlet through the interior passage of the tubular member, and a closed position, in which the outer wall of the tubular member occludes the cannula outlet thereby preventing fluid communication between the housing outlet opening and the cannula outlet.

18. The device of claim 17, further comprising:
a biasing device adjacent the tubular member for resiliently urging the tubular member to the closed position.

19. A method, comprising:
surgically implanting a device that includes:
a housing having an inlet opening, an outlet opening and an interior conduit defined therein between the inlet opening and the outlet opening; and
a manipulatable housing valve positioned between the inlet opening and the outlet opening for selectively permitting fluid communication between the inlet opening and the outlet opening,
wherein the housing valve includes an elongate member supported within the housing, the elongate member being movable between an open position, in which fluid communication is permitted between the inlet opening and the outlet opening, and a closed position, in which the elongate member occludes fluid communication between the inlet opening and the outlet opening,
wherein at least one end of the elongate member protrudes through an external surface of the housing, the at least one end of the elongate member being subcutaneously manipulatable for moving the elongate member between the open and closed positions,
wherein the elongate member includes a transverse bore formed therethrough, the bore aligning with the interior conduit when the elongate member is in the open position for permitting fluid communication between the inlet opening and the outlet opening, wherein the elongate member has a non-circular cross section, and
wherein the elongate member is supported within a support hole of the housing that has a non-circular cross-section corresponding in shape to that of the elongate member, the correspondingly shaped cross-sections of the elongate member and the support hole preventing a misalignment of the transverse bore and the interior conduit in the open position.

20. A method, comprising:
surgically implanting a device that includes:
a housing having an inlet opening, an outlet opening and an interior conduit defined therein between the inlet opening and the outlet opening; and a manipulatable housing valve positioned between the inlet opening and the outlet opening for selectively permitting fluid communication between the inlet opening and the outlet opening, wherein the housing valve includes an elongate member supported within the housing, the elongate member being movable between an open position, in which fluid communication is permitted between the inlet opening and the outlet opening, and a closed position, in which the elongate member occludes fluid communication between the inlet opening and the outlet opening, wherein at least one end of the elongate member protrudes through an external surface of the housing, the at least one end of the elongate member being subcutaneously manipulatable for moving the elongate member between the open and closed positions, wherein the elongate member includes a transverse bore formed therethrough, the bore aligning with the interior conduit when the elongate member is in the open position for permitting fluid communication between the inlet opening and the outlet opening, wherein the elongate member has a non-circular cross section, and wherein the elongate member is inserted through an opening of a retaining clip attached to the housing, the opening of the retaining having a non-circular cross-section corresponding in shape to that of the elongate member, the correspondingly shaped cross-sections of the elongate member and the retaining clip opening preventing a misalignment of the transverse bore and the interior conduit in the open position.

* * * * *